(12) United States Patent
Kilgour et al.

(10) Patent No.: US 6,262,170 B1
(45) Date of Patent: *Jul. 17, 2001

(54) SILICONE ELASTOMER

(75) Inventors: John A. Kilgour, Clifton Park; An-Li Kuo, Chappaqua, both of NY (US)

(73) Assignee: General Electric Company, Pittsfield, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/211,736

(22) Filed: Dec. 15, 1998

(51) Int. Cl.$^7$ ....................................... C08K 5/24
(52) U.S. Cl. ................. 524/731; 524/862; 524/837; 528/15; 528/25; 424/401; 424/65
(58) Field of Search ............... 528/15, 25; 424/401, 424/65; 524/731, 837, 862

(56) References Cited

U.S. PATENT DOCUMENTS

| | | | |
|---|---|---|---|
| 2,823,218 | 2/1958 | Spier et al. | 260/448.2 |
| 3,159,601 | 12/1964 | Ashby | 260/46.5 |
| 3,159,662 | 12/1964 | Ashby | 260/448.2 |
| 3,775,452 | 11/1973 | Karstedt | 260/429 R |
| 4,526,953 * | 7/1985 | Dallavia, Jr. | 528/15 |
| 4,689,248 * | 8/1987 | Traver et al. | 427/168 |
| 4,853,474 * | 8/1989 | Bahr et al. | 556/445 |
| 4,987,169 | 1/1991 | Kuwata et al. . | |
| 5,066,714 | 11/1991 | Inoue et al. | 524/731 |
| 5,387,417 * | 2/1995 | Rentsch | 424/401 |
| 5,506,289 | 4/1996 | McDermott et al. | 524/306 |
| 5,529,837 | 6/1996 | Fujiki et al. | 428/266 |
| 5,571,853 | 11/1996 | Ikeno et al. | 524/268 |
| 5,654,362 * | 8/1997 | Schulz, Jr. et al. | 524/862 |
| 5,654,389 * | 8/1997 | Raleigh | 528/15 |
| 5,674,966 | 10/1997 | McDermott et al. | 528/32 |
| 5,698,654 | 12/1997 | Nye et al. | 528/21 |
| 5,717,010 | 2/1998 | Ward et al. | 523/213 |
| 5,741,439 * | 4/1998 | Armstrong et al. | 252/312 |
| 5,760,116 | 6/1998 | Kilgour et al. . | |
| 5,929,164 * | 7/1999 | Zhang | 524/862 |
| 5,977,280 * | 11/1999 | Kadlec et al. | 528/15 |

FOREIGN PATENT DOCUMENTS 0869142A 10/1998 (EP) .
WO 98/18849 5/1998 (WO) .

* cited by examiner

*Primary Examiner*—Margaret G. Moore

(57) ABSTRACT

The cross-linked hydrosilylation reaction product of an alkenyl functional silicone compound, a silylhydride functional silicone compound; and one or more α,β-unsaturated alkenes exhibits hydrolytic stability, compatibility with organic solvents and is useful as a component in personal care compositions.

34 Claims, No Drawings

SILICONE ELASTOMER

FIELD OF THE INVENTION

The present invention relates to silicone polymers, more specifically to alkyl substituted silicone elastomers.

BACKGROUND OF THE INVENTION

Silicone compositions comprising a silicone fluid and a cross-linked silicone elastomer are known, see for example, U.S. Pat. No. 4,987,169, coassigned U.S. Pat. Nos. 5,760,116; 4,987,169. Neither U.S. '169 patent nor the U.S. '116 patent disclose dispersions of the silicone elastomer in fluids other than silicone fluids.

WO 98/18849 discloses fatty alcohol or aliphatic glycol-grafted silicone gels having enhanced oil compatibility. The grafted substituents are attached to the silicone gel via Si—O—C bonds, which are readily susceptible to hydrolysis in the presence of moisture.

What is needed in a hydrolytically stable silicone elastomer that is compatible with media, such as hydrocarbons, other than silicone fluids.

SUMMARY OF THE INVENTION

In a first aspect, the present invention is directed to a cross-linked alkyl substituted silicone elastomer, comprising the cross-linked hydrosilylation reaction product of:

(i) an alkenyl functional silicone compound;
(ii) a silylhydride functional silicone compound; and
(iii) one or more $\alpha,\beta$-ethylenically unsaturated alkenes.

The silicone elastomer is hydrolytically stable, in that the alkyl substituents are attached to the elastomer via Si—C bonds having good hydrolytic stability and can be easily and economically prepared in a single step. As used herein, the terminology "hydrolytically stable" means a tendency not to undergo changes in structure, such as, for example, cleavage of bonds, as a result of exposure to moisture.

In a second aspect, the present invention is directed to a method for making a cross-linked alkyl substituted silicone elastomer, comprising forming the hydrosilylation reaction product of:

(i) an alkenyl functional silicone compound;
(ii) a silylhydride functional silicone compound; and
(iii) one or more $\alpha,\beta$-ethylenically unsaturated alkenes.

In a third aspect, the present invention is directed to a silicone composition, comprising a liquid medium, said liquid medium comprising an organic liquid, a silicone fluid or a mixture thereof; and a silicone elastomer of the present invention dispersed in the liquid medium. The elastomer of the present invention exhibits improved compatibility with organic liquids. As used herein, the "compatibility" of an elastomer with a liquid refers to the ability to form a stable dispersion of the elastomer in organic liquid.

In a fourth aspect, the present invention is directed to an emulsion comprising an emulsion of a first liquid phase and a second liquid phase and a silicone elastomer of the present invention dispersed in the emulsion.

In a fifth aspect, the present invention is directed to a personal care composition comprising a silicone elastomer of the present invention.

DETAILED DESCRIPTION OF THE INVENTION

Silicone Elastomer

In preferred embodiment, the cross-linked alkyl substituted silicone elastomer of the present invention comprises the cross-linked hydrosilylation reaction product of, based on 100 parts by weight ("pbw") of the combined alkenyl functional silicone compound, silylhydride functional silicone compound and $\alpha,\beta$-ethylenically unsaturated alkenes, from 10 pbw to 99.9 pbw, more preferably from 40 pbw to 99.5 pbw, even more preferably from 65 pbw to 95 pbw of the combined alkenyl functional silicone compound and silylhydride functional silicone compound and from greater than 0.1 pbw to 90 pbw, more preferably from 0.5 pbw to 60 pbw, even more preferably from 5 pbw to 35 pbw of the one or more $\alpha,\beta$-ethylenically unsaturated alkenes.

In a preferred embodiment, the alkyl substituted silicone elastomer of the present invention forms a cross-linked three dimensional network that does not dissolve in, but is capable of being swollen by a suitable liquid medium, such as for example, a low molecular weight silicone or an organic liquid. The amount of crosslinking present in the cross-linked silicone elastomer network may be characterized with respect to the degree of swelling exhibited by the network in the liquid medium. In a preferred embodiment, the cross-linked structure of the silicone elastomer is effective to allow the network to be swollen by a low molecular weight silicone fluid, as defined more fully below, from its original volume to a swollen volume that is a factor of from 1.01 to 5000, more preferably from 2 to 1000, and even more preferably from 5 to 500, times its original volume.

The cross-linked alkyl substituted silicone elastomer of the present invention may be formed by each of several alternative methods.

In a first embodiment, the silylhydride functional silicone compound and one or more $\alpha,\beta$-ethylenically unsaturated alkenes are contacted under hydrosilylation conditions to form an alkyl substituted silylhydride functional silicone compound and the alkyl substituted silylhydride functional silicone compound is subsequently contacted under hydrosilylation conditions with the alkenyl functional silicone compound to form the a cross-linked alkyl substituted silicone elastomer of the present invention.

In a second, and preferred, embodiment, the alkenyl functional silicone compound, and silylhydride functional silicone compound and the one or more $\alpha,\beta$-ethylenically unsaturated alkenes are contacted under hydrosilylation conditions to form the a cross-linked alkyl substituted silicone elastomer of the present invention.

In a third embodiment, the alkenyl functional silicone compound, and silylhydride functional silicone compound are contacted under hydrosilylation conditions to form a silicone elastomer gel and the gel is subsequently contacted under hydrosilylation conditions with the one or more $\alpha,\beta$-ethylenically unsaturated alkenes to form the a cross-linked alkyl substituted silicone elastomer of the present invention.

In a preferred embodiment the alkenyl functional silicone compound comprises one or more compounds of the formula (I):

$$M_a M^{vi}_b D_c D^{vi}_d T_e T^{vi}_f Q_g \qquad (I)$$

wherein:
M is $R^1 R^2 R^3 SiO_{1/2}$;
$M^{vi}$ is $R^4 R^5 R^6 SiO_{1/2}$;
D is $R^7 R^8 SiO_{2/2}$;
$D^{vi}$ is $R^9 R^{10} SiO_{2/2}$;
T is $R^{11} SiO_{3/2}$;
$T^{vi}$ is $R^{12} SiO_{3/2}$; and
Q is $SiO_{4/2}$;

$R^1$, $R^2$, $R^3$, $R^7$, $R^8$ and $R^{11}$ are each independently alkyl, preferably $(C_1-C_{60})$alkyl, aryl or aralkyl;

$R^4$, $R^9$ and $R^{12}$ are each independently monovalent terminally unsaturated hydrocarbon radicals;

$R^5$, $R^6$ and $R^{10}$ are each independently monovalent terminally unsaturated hydrocarbon radicals, alkyl, aryl or aralkyl, preferably $(C_1-C_{60})$alkyl, aryl or aralkyl, more preferably $(C_1-C_{60})$alkyl;

a, b, c, d, e, f and g are each integers wherein: a, b, e, f, and g are each greater than or equal to 0 and less than or equal to 50, $0 \leq c \leq 2000$, $0 \leq d \leq 200$, and provided that: $(a+b) \leq (2+3e+3f+4g)$ and $1.5 \leq (b+d+f) \leq 200$.

In a highly preferred embodiment, $R^4$ is a monovalent terminally unsaturated $(C_2-C_6)$hydrocarbon radical; $R^5$, $R^6$, $R^7$ and $R^8$ are each independently $(C_1-C_6)$alkyl; $R^5$, $R^6$, $R^7$ and $R^8$ are each independently $(C_1-C_6)$alkyl; b is 2; $100 \leq c \leq 2000$; and a, d, e, f and g are each 0.

In a preferred embodiment, the silylhydride functional silicone compound comprises one or more compounds of the formula (II):

$$M_h M^H_i D_j D^H_k T_l T^H_m Q_n \quad \text{(II)};$$

M, D, T and Q are each defined as above $M^H$ is $R^{13}R^{14}R^{15}SiO_{1/2}$;

$D^H$ is $R^{16}R^{17}SiO_{2/2}$;

$T^H$ is $R^{18}SiO_{3/2}$;

$R^1$, $R^2$, $R^3$, $R^7$, $R^8$ and $R^{11}$ are each independently alkyl, aryl or aralkyl;

$R^{13}$, $R^{16}$ and $R^{18}$ are each independently H;

$R^{14}$, $R^{15}$ and $R^{17}$ are each independently H, alkyl, aryl or aralkyl, preferably $(C_1-C_{60})$alkyl, aryl or aralkyl, more preferably $(C_1-C_{60})$alkyl; and h, i, j, k, l, m, and n are each integers wherein:

h, i, l, m and n are each greater than or equal to 0 and less than or equal to 50, $0 \leq j \leq 2000$, $0 \leq k \leq 200$, and provided that: $(h+i) \leq (2+3l+3m+4n)$ and $1.5 \leq (i+k+m) \leq 200$.

In a highly preferred embodiment, $R^{14}$ and $R^{15}$ are each independently $(C_1-C_6)$alkyl, and more preferably are each methyl; $R^{13}$ is H; $4 \leq i \leq 30$; $1 \leq n \leq 15$ and h, j, k, l and m are each 0. In an alternative highly preferred embodiment, $R^{14}$, $R^{15}$ and $R^{17}$ are each independently $(C_1-C_{12})$alkyl, $R^{13}$ and $R^{16}$ are each H; h+i=2, $0 \leq j \leq 100$, $2 \leq k \leq 100$ and l, m and n are each 0.

Suitable monovalent terminally unsaturated hydrocarbon radicals include monovalent linear or branched terminally unsaturated hydrocarbon groups. In a preferred embodiment, the terminally unsaturated hydrocarbon radicals are selected from linear or branched terminally unsaturated alkenyl groups containing from 2 to 10 carbon atoms per group, such as, for example, ethenyl, 2-propenyl, 1-methylethenyl, 2-methyl-2-propenyl, ethenylphenyl, and 3-butenyl, 7-octenyl, more preferably ethenyl, 2-propenyl.

Suitable monovalent alkyl groups include linear or branched alkyl groups. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl, stearyl, cetyl, eicosyl, tridecyl, hexadecyl.

As used herein, the term "aryl" means a monovalent unsaturated hydrocarbon ring system containing one or more aromatic rings per group, which may optionally be substituted on the one or more aromatic rings with one or more alkyl groups, each preferably containing from 2 to 6 carbon atoms per alkyl group and which, in the case of two or more rings, may be fused rings. Suitable monovalent aromatic hydrocarbon radicals include, for example, phenyl, tolyl, 2,4,6-trimethylphenyl, 2-isopropylmethylphenyl, 1-pentalenyl, naphthyl, anthryl.

Aralkyl includes, for example, phenylethyl, 2-(1-naphthyl)ethyl.

Suitable α,β-ethylenically unsaturated alkenes include linear or branched α,β-unsaturated alkenes, which may, optionally, contain more than one unsaturated site per molecule. In a preferred embodiment, the α,β-ethylenically unsaturated alkenes are selected from the α,β-ethylenically unsaturated alkenes containing from 2 to 60 carbon atoms per molecule, such as, for example, ethene, propene, 2-methylpropene, 1-butene, 1,3-butadiene, 1-pentene, 2-methyl-1,3-butadiene, 1-dodecene, $H_2C=CH(CH_2)_{13}CH_3$, $H_2C=CH(CH_2)_{15}CH_3$, $H_2C=CH(CH_2)_{50}CH_3$. In a preferred embodiment, the one or more α,β-ethylenically unsaturated alkenes are selected from α,β-ethylenically unsaturated $(C_4-C_{24})$alkenes.

In a preferred embodiment, the silicone elastomer of the present invention is made bay contacting one or more alkenyl functional compounds according to formula (I) with one or more silylhydride functional silicone compounds according to structural formula (II) and one or more α,β-ethylenically unsaturated alkenes under hydrosilylation conditions.

As used herein, the terminology "$(C_n-C_m)$", wherein n and m are each integers, in reference to an organic compound or substituent group means that the compound or group contains from n to m carbon atoms per molecule of the compound or per group. As used herein, the terminology "each independently selected from" in reference to organic substituents on an organosiloxane repeating unit of a polyorganosiloxane polymer means that each substituent group is selected independently from other substituent groups on the repeating unit and independently from the substituent groups on any other analogous repeating units of the polymer. A polyorganosiloxane polymer described herein as including more than one of a particular type of organosiloxane repeating unit, for example, diorganosiloxane ("D") units, wherein the substituents on the units are "each independently selected" from a defined group includes both polyorganosiloxane homopolymers, that is, wherein the substituents on each of the organosiloxane repeating units of the polymer are the same substituents, such as, for example, a polydimethylsiloxane polymer, as well as polyorganosiloxane copolymers, that is, a polymer containing two or more analogous organosiloxane repeating units, each bearing different substituents, such as, for example, a poly (dimethylsiloxane/methylphenylsiloxane) copolymer.

In a highly preferred embodiment, $R^4$ is a monovalent terminally unsaturated $(C_2-C_6)$hydrocarbon radical, more preferably, ethenyl or 2-propenyl, more preferably ethenyl; $R^5$, $R^6$, $R^7$ $R^8$, $R^{14}$ and $R^{15}$ are each independently $(C_1-C_6)$ alkyl, and more preferably are each methyl; $R^{13}$ is H; b is 2; $100 \leq c \leq 2000$; preferably $500 \leq c \leq 1500$; $4 \leq i \leq 30$; $1 \leq n \leq 15$ and a, d, e, f g, h, j, k, l and m are each 0.

In an alternative highly preferred embodiment, $R^4$ is a monovalent terminally unsaturated $(C_2-C_6)$hydrocarbon radical, more preferably, ethenyl or 2-propenyl, more preferably ethenyl; $R^1$, $R^2$, $R^3$, $R^5$, $R^6$, $R^7$ $R^8$, $R^{14}$, $R^{15}$ and $R^{17}$ are each independently $(C_1-C_{12})$alkyl, more preferably $(C_1-C_{12})$alkyl, still more preferably methyl, $R^{13}$ and $R^{16}$ are each H; b is 2; $100 \leq c \leq 2000$; preferably $500 \leq c \leq 1500$; h+i=2, $0 \leq j \leq 100$, $2 \leq k \leq 100$ and a, d, e, f, g, l, m and n are each 0.

Suitable alkenyl functional silicone compounds and silylhydride functional silicone compounds are described in, for example, U.S. Pat. Nos. 5,506,289; 5,674,966; 5,717,010; 5,571,853; and 5,529,837, the disclosures of which are each hereby incorporated by reference herein. The alkenyl functionality and the silylhydride functionality may be combined into one molecule self-curing molecule or compound, such as, for example, as disclosed in U.S. Pat. No. 5,698,654.

In a preferred embodiment, the hydrosilylation reaction is carried out in the presence of a hydrosilylation catalyst. Suitable catalysts are known, as described in, for example, U.S. Pat. Nos. 2,823,218; 3,159,601; 3,159,662; and 3,775,452, and include, for example, ruthenium, osmium, rhodium, iridium, palladium and platinum hydrosilylation catalysts.

In a preferred embodiment, the hydrosilylation reaction is carried out in a reaction medium comprising one or more silicone fluids, one or more organic liquids, each as more fully described below, or a mixture thereof.

Processing

The crosslinked silicone elastomer of the present invention may then be further swollen with additional solvent, which may be either the same as or different from the reaction medium used in making the crosslinked silicone polymer. The swollen crosslinked silicone elastomer is then subjected to shear force, for example, using a two-roll mill, a homogenizer or a high shear mixer, to break the elastomer into particles.

In a preferred embodiment, the swollen silicone elastomer is subjected high flow induced shear by forcing the elastomer through an orifice at high pressure. In a preferred embodiment, the viscosity of the swollen elastomer should be greater than 500 centiStokes ("cStk"), more preferably greater than 750 cStk, still more preferably greater than 1000 cStk and most preferably over 5000 cStk. The orifice size is limited by the ability of the pumping system to maintain sufficient pressure. In a preferred embodiment, the orifice area is less than 0.5 square inches ("in$^2$"), preferably less than 0.1 in$^2$, more preferably less than 0.05 in$^2$, and most preferably less than 0.01 in$^2$. In a preferred embodiment, the pressure is above 500 pounds per square inch ("psi"), more preferably above 1000 psi, still more preferably, over 1500 psi and most preferably over 2000 psi.

Silicone Compositions

In a preferred embodiment, the silicone composition of the present invention comprises, based on 100 pbw of the composition, from 1 pbw to 99 pbw, more preferably from 5 pbw to 95 pbw, and even more preferably 10 pbw to 90 pbw of the liquid medium, from 1 pbw to 99 pbw, more preferably from 5 pbw to 95 pbw, and even more preferably 10 pbw to 90 pbw of the silicone particles.

In a preferred embodiment, the liquid medium consists essentially of an organic liquid, more preferably a substantially non-polar organic liquid. In an first alternative preferred embodiment, the liquid medium consists of a silicone fluid. In a second alternative preferred embodiment, the liquid medium comprises an organic liquid, more preferably a substantially non-polar organic liquid, and a silicone fluid that is miscible with the organic liquid.

Silicone Emulsions

In a preferred embodiment, the silicone emulsion of the present invention comprises, based on 100 pbw of the combined amount of the first and second liquids, from 0.1 pbw to 99.1 pbw, more preferably from 5 pbw to 95 pbw and even more preferably from 15 pbw to 85 pbw, of the first liquid and from 0.1 pbw to 99.1 pbw, more preferably from 5 pbw to 95 pbw and even more preferably from 15 pbw to 80 pbw, of the second liquid and, based on 100 pbw of the silicone emulsion, from 0.001 pbw to 75 pbw, more preferably from 0.01 pbw to 40 pbw and even more preferably from 0.05 pbw to 20 pbw, of the silicone elastomer of the present invention.

In a first highly preferred embodiment of the silicone emulsion of the present invention, the first liquid phase is a continuous phase and the second liquid phase is a discontinuous phase emulsified with the continuous first liquid phase. In an alternative highly preferred embodiment of the silicone emulsion of the present invention, the second liquid phase is a continuous phase and the first liquid phase is a discontinuous phase emulsified with the continuous second liquid phase.

In a preferred embodiment, the first liquid comprises a silicone fluid, a substantially non-polar organic liquid, or a mixture thereof and the second liquid comprises water, a substantially polar organic liquid or a mixture thereof.

In a preferred embodiment, the silicone emulsion of the present invention further comprises one or more emulsifying agents. Suitable emulsifying agents useful in preparing the emulsions of the present include, for example, silicone-containing emulsifying agents, emulsifying agents derived from sorbitan compounds and emulsifying agents derived from fatty alcohols, more preferably the emulsifying agent is selected from the group consisting of fatty acid esters, sorbitan sesquioleate, sorbitan oleate, sorbitan isostearate, polyglyceryl-3 oleate, alkoxylated alcohols such as laureth-4, laureth-7, deceth-12, steareth-10, hydroxylated or alkoxylated derivatives of silicone compounds such as dimethicone copolyol, cetyl dimethicone copolyol, and lauryl methicone copolyol, glyceryl esters such as polyglyceryl-4-isostearyl and mixtures thereof.

The first liquid, second liquid and silicone elastomer are mixed together to form the silicone emulsion of the present invention. Preferably, the components of the disperse phase is added to the components of the continuous phase while subjecting the mixture of components to low shear mixing and the mixture so formed is then subjected to high shear mixing. In a preferred embodiment, a dispersion of the silicone elastomer of the present invention in the first liquid is slowly added to the second liquid while subjecting the combined phases to low shear mixing, such as, for example, in a mixing tank equipped with a propeller-type stirrer, and then the mixture so formed is subjected to high shear mixing, for example, in a Sonolator apparatus, a Gaullen homogenizer or other high shear mixer, such as an Eppenbach Mixer, to form the silicone emulsion. In a more highly preferred embodiment, an emulsifying agent is combined with the first liquid prior to adding the components of the first phase to the components of the second phase.

Silicone Fluid

Silicone fluids suitable for use as the silicone fluid component of the composition of the present invention are those organosilicon compounds that are in the liquid state at or near room temperature, for example, from about 20° C. about 50° C., and about one atmosphere pressure. In a preferred embodiment, the silicone fluid component of the composition of the present invention having a viscosity of below about 1,000 centistokes, preferably below about 500 centistokes, more preferably below about 250 centistokes, and most preferably below 100 centistokes, at 25° C. Suitable silicone fluids include, for example, cyclic silicones of the formula $D_r$, wherein D is defined as above, $R^7$ and $R^8$ are each preferably methyl, and r is an integer wherein $3 \leq r \leq 12$, such as, for example, hexamethylcyclotrisiloxane ("$D_3$"), octamethylcyclotetrasiloxane ("$D_4$"), decamethylcyclopentasiloxane ("$D_5$"), and dodecamethylcyclohexasiloxane ("$D_6$") as well as linear organopolysiloxanes having the formula (III):

$$M'D'_sM' \qquad (III)$$

wherein:
M' is $R^{19}R^{20}R^{21}SiO_{1/2}$;
D' is $R^{22}R^{23}SiO_{2/2}$;
$R^{19}$, $R^{20}$, $R^{21}$, $R^{22}$ and $R^{23}$ are each independently alkyl, aryl or aralkyl;
s is an integer of from 0 to 300, wherein $0 \leq s \leq 300$, preferably $0 \leq s$ 100, more preferably $0 \leq s \leq 50$, and most preferably $0 \leq s \leq 20$.

Organic Liquid

Suitable organic liquids include any organic compound that is in the liquid state at or near room temperature, for example, from about 20° C. about 50° C., and about one atmosphere pressure, that is substantially inert to the silicone phase, that is, does not undergo a chemical reaction with any of the components of the silicone phase, under the anticipated conditions of processing and use and that is suitable for use in the intended end-use application, such as, for example, a cosmetic composition, to be prepared from the non-aqueous silicone composition of the present invention.

As used herein, the terminology "substantially non-polar" means exhibiting a dipole moment of less than about 0.9. Suitable substantially non-polar organic liquids include, for example, linear or branched hydrocarbon liquids, such as, for example, isododecane, hexadecane and octadecane, natural oils, such as, for example, coconut oil, almond oil, apricot oil, mineral oils castor oil and soybean oil, fatty alcohols such as octadecanol, dodecanol or stearyl alcohol, fatty acids, such as, for example, stearic acid, lauric acid, palmitic acid, esters, such as, for example, ($C_{12}$–$C_{15}$) alkylbenzoates, hexyl laurate, decyl stearate and glyceryl trioctanoate, as well as mixtures of two or more of any of the above.

In a highly preferred embodiment, the substantially non-polar organic liquid comprises a hydrocarbon liquid, more preferably a ($C_{10}$–$C_{24}$)alkane.

As used herein, the terminology "substantially polar" means exhibiting a dipole moment of from about 0.9 to 4.5. Suitable substantially polar organic liquids include organic hydroxylic liquids, such as, for example, alcohols, glycols, polyhydric alcohols and polymeric glycols. More preferably, the substantially polar organic liquid is selected from of alcohols including polyhydric alcohols, glycols, including polymeric glycols, and mixtures thereof. Preferably, the substantially polar organic liquid contains an ($C_1$–$C_{12}$) alcohol, such as, for example, ethanol, propyl alcohol and iso-propyl alcohol, a ($C_2$–$C_{12}$)glycol, such as for example, ethylene glycol, propylene glycol, dipropylene glycol, tripropylene glycol, butylene glycol, iso-butylene glycol and methyl propane diol, a polyhydric alcohol, such as for example, glycerin erythritol and sorbitol, or a polymeric glycol, such as for example, polyethylene glycol, polypropylene glycol mono alkyl ethers and polyoxyalkylene copolymers. In a highly preferred embodiment, the substantially polar organic liquid is selected from ethanol, propyl alcohol, iso-propyl alcohol, ethylene glycol, propylene glycol, dipropylene glycol, tripropylene glycol, butylene glycol, iso-butylene glycol, methyl propane diol, glycerin, erythritol sorbitol, polyethylene glycol, polypropylene glycol mono alkyl ethers, polyoxyalkylene copolymers.

Personal Care Compositions

The personal care applications where the silicone elastomer of the present invention may be employed include, but are not limited to, deodorants, antiperspirants, skin lotions, moisturizers, hair care products such as shampoos, mousses and styling gels, protective creams such as sunscreen and anti-aging products, color cosmetics such as lipsticks, foundations, blushes, makeup, and mascaras and other cosmetic formulations where silicone components have been conventionally been added, as well as drug delivery systems for topical application of medicinal compositions that are to be applied to the skin.

Suitable personal care compositions are made by combining, in a manner known in the art, such as, for example, by mixing, one or more of the above components with the silicone elastomer of the present invention, the silicone composition of the present invention or the silicone emulsion of the present invention. Suitable personal care compositions may be in the form of a single phase or in the form of an emulsion, including oil-in-water, water-in-oil and anhydrous emulsions.

In a preferred embodiment, an antiperspirant composition comprises one or more active antiperspirant agents, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, and the silicone elastomer of the present invention.

In a preferred embodiment, a skin care composition comprises silicone elastomer of the present invention, and optionally, further comprises a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, vitamin C and vitamin E, sunscreen or sunblock compounds, such as for example, titanium dioxide, oxybenzone sunscreens and p-aminobenzoic acid.

In a preferred embodiment, a personal care composition comprises a non-aqueous emulsion of the silicone elastomer of the present invention and one or more water-sensitive dermatological active agents or cosmetic active agents, such as for example, ascorbic acid or an enzyme, particularly a protease, such as, for example, enzyme sold under the trade name SUBTILISIN SP 544 by Novo Nordisk or the enzyme sold under the trade name LYSOVEG by Laboratoires Serobiologiques de Nancy.

The personal care composition of the present invention may, optionally, further contain such know components as, for example, emollients, moisturizers, humectants, pigments, colorants, fragrances, biocides, preservatives, exfoliants, hormones, enzymes, medicinal compounds, antimicrobial agents, anti-fungal agents, vitamins, salts, electrolytes, alcohols, polyols, absorbing agents for ultraviolet radiation, botanical extracts, surfactants, silicone oils, organic oils, waxes, thickening agents such as, for example, fumed silica or hydrated silica, clays, such as, for example, bentonite, and organo-modified clays.

EXAMPLES 1 AND 2 AND COMPARATIVE EXAMPLE 1

The silicone elastomer of Example 1 is made by combining: (i) 2000 grams of divinyl siloxanes of the average formula $M^{vi}_2D_{900}$, wherein $M^{vi}$ and D are each defined as for formula (I) above; $R^4$ is ethenyl; and $R^5$, $R^6$, $R^7$ and $R^8$ are each methyl; (ii) 23.0 grams of silylhydride functional resins of the average formula $(M^H_2Q)_4$, wherein $M^H$ and Q are each defined as for formula (II) above, $R^{13}$ is H and $R^{14}$ and $R^{15}$ are each methyl; and (iii) 36 grams of mixed α, β-ethylenically unsaturated ($C_{16}$–$C_{18}$) alkenes with 6000 grams of $D_5$ in 10 liter mixer. A hydrosilylation catalyst (0.4 grams of 10% platinum catalyst solution) was then added to the reactor. The contents of the reactor were then stirred and heated to 80° C. over 7 hours. The polymerized solid product, in the form of a fluffy white powder, was then removed from the reactor, diluted to 4.75 wt % solids with $D_5$ and subjected to high shear in a Sonolator homogenizer (orifice size=0.0007 in$^2$) for four passes at 4500 psi to produce a clear gel.

The silicone elastomer of Example 2 is made by combining (i) 2000 grams of the divinyl siloxanes described above in Example 1, (ii) 97 grams of linear silylhydride-functional resins of the average formula $M_2D_{22}D^H{}_{22}$, wherein: M, D and $D^H$ are each defined as for formula (II) to above, $R^{16}$ is H and $R^1$, $R^2$, $R^3$, $R^7$, $R^8$, $R^{13,}$ $R^{14}$, $R^{15}$ and $R^{17}$ are each methyl, and (iii) 43 grams of mixed α,β-ethylenically unsaturated ($C_{16}$–$C_{18}$) alkenes with 6000 grams of $D_5$ in a 10 liter mixer. The mixture was stirred and 5 ppm of platinum catalyst was added. The reaction was heated to 80° C. over 7 hours. The product was then diluted to about 6.05% polymer content and then subjected to high shear in a Sonolator® homogenizer for four passes at 4500 psi to generate a clear gel.

The composition of Comparative Example C1 was made by a process analogous to that described above for the elastomer of Example 1 except that the mixed ($C_{16}$–$C_{18}$) olefins were omitted from the reaction mixture. The reaction product was diluted to 5.5 wt % solids with $D_5$ and subjected to high shear in a Sonolator homogenizer for four passes at 4500 psi to produce a clear gel.

Each of the compositions of Examples 1 and 2 and Comparative Example C1 were mixed with isododecane.

A sample of 50 pbw of the composition of Example 1 was diluted with 50 pbw isododecane to form a visually clear mixture having a viscosity of 12,500 ctks, with no evidence of precipitation of gel particles.

A sample of 50 pbw of the composition of Example 2 was blended with 30% added isododecane. The resulting visually clear gel had a viscosity of 15,500 cSt.

A sample of the composition of Comparative Example C1 was also diluted with isodecane. As isododecane is added to and mixed with the composition of Comparative Example C1, the viscosity of the mixture so formed falls rapidly to less than 100 cSt at about 30% added isododecane. Small particles were observed on the sides of the flask.

These results observed for mixtures of isododecane with the compositions of Examples 1 and 2 demonstrate the compatibility of the alkyl substituted elastomers with the isododecane, i.e., it appears that the isododecane is able to further swell the elastomeric particle to thereby maintain the viscosity of the dispersion relatively stable. The clear visual appearance of the dispersions provide further indication of compatibility of the alkyl substituted elastomers with the isododecane.

The results observed for Comparative Example C1 indicate that the isododecane is not compatible with the elastomer of Comparative Example C1, but rather appears to be drawing D5 from the elastomer particles, resulting in a dramatic decrease in the viscosity of the mixture. Furthermore, the small particles were observed on the sides of the flask, indicate precipitation of the elastomer from the isododecane/$D_5$ solution.

EXAMPLES 3–8 AND COMPARATIVE EXAMPLES C2–C6

A silicone polymer was made by adding 182 pbw of a silicone resin having an average formula of $(MH_2Q)_4$, 2000 pbw of a 40000 cSt terminally substituted divinylpolysiloxane 276 pbw of ($C_{24}$–$C_{28}$)α-olefin and 6000 pbw of decamethylcyclopentasiloxane to reaction vessel. A platinum catalyst (0.42 pbw of 10% solution) was added to the reaction vessel and the contents of the reaction vessel were then mixed and heated to 80° C. over 7 hours. The product so formed was then removed from the reaction vessel and diluted with additional decamethylcyclopentasiloxane until the polymer solids concentration was 5.5%. The diluted product was then subjected to high shear in a Sonolator homogenizer for three passes at 4500 psi, to give a clean, high viscosity gel.

The composition of Example 4 was made by diluting the gel of Example 3 with 20% by weight of isohexadecane. The isohexadecane was absorbed to produce a clear gel with viscosity of 60,000 cSt.

The composition of Comparative Example C2 was made by diluting Comparative Example C1 with 20% by weight of isohexadecane. The resulting mixture was a cloudy, free flowing liquid with a viscosity of less than 100 cSt.

The composition of Example 5 was made by diluting the gel of Example 3 with 20% by weight of ($C_{24}$–$C_{28}$)α-olefin. Upon heating to the olefin melting point, the mixture formed a clear solution and upon cooling, the product mixture was a homogeneous, low melting soft waxy solid that spreads easily onto the skin.

The composition of Comparative Example C3 was made by diluting Comparative Example C1 with 20% by weight of ($C_{24}$–$C_{28}$)α-olefin. Upon heating to the melting point of the wax, a cloudy, heterogeneous mixture consisting of large domains of wax and silicone elastomer was formed. On cooling, a heterogeneous mixture of elastomer and wax was formed.

The composition of Example 6 was made by diluting the gel of Example 3 with 30% by weight of hydrogenated polyisobutene. The hydrogenated polyisobutene was to produce a clear, homogeneous gel with a viscosity of greater than 4000 cSt.

The composition of Comparative Example C4 was made by diluting Comparative Example C1 with 30% by weight of hydrogenated polyisobutene. The resulting mixture was a free flowing liquid of 988 cSt.

The composition of Example 7 was made by diluting the gel of Example 3 with 20% by weight of stearyl alcohol. Upon heating to melting point of the stearyl alcohol, the stearyl alcohol was absorbed by the elastomer and produced a visually clear solution. Upon cooling, the product mixture was a homogeneous, low melting soft solid that spreads easily onto the skin.

The composition of Comparative Example C5 was made by diluting Comparative Example C1 with 20% by weight of stearyl alcohol. Upon heating to the melting point of the stearyl alcohol, a cloudy heterogeneous solution was formed. On cooling, the stearyl alcohol solidified to form a heterogeneous mixture of stearyl alcohol particles and siloxane.

The composition of Example 8 was made by diluting the gel of Example 3 with 20% by weight of isostearic acid. The isostearic acid was absorbed to produce a clear, homogeneous gel with a viscosity of 76,000 cSt.

The composition of Comparative Example C6 was made by diluting Comparative Example C1 with 20% by weight isostearic acid. The resulting mixture was a cloudy, free flowing liquid of less than 100 cSt.

EXAMPLE 9

The make-up foundation composition of Example 9 is made by combining the listed components in the relative amounts (in pbw) set forth below in TABLE I.

TABLE I

| | |
|---|---|
| Oil Phase | |
| Cyclopentasiloxane and dimethicone copolyol | 10 |
| Silicone elastomer of Example 1 | 10 |
| C30–45 Alkyl Dimethicone | 2 |
| Cyclopentasiloxane ( | 20 |
| Bis-Phenyl Propyl Dimethicone | 10 |
| Sorbitan Oleate | 0.5 |
| Pigment dispersion WE (Kobo) | 5 |
| Water Phase | |
| Water | 42.3 |
| Polysorbate 20 | 0.2 |
| NaCl | 1 |

The silicone phase and water phase are made separately. The components of the silicone phase are added to a mixing vessel in the order listed and mixed together with moderate agitation. The components of the water phase are added to a mixing vessel in the order listed and mixed together with moderate agitation. The water phase is then added to the silicone phase at a rate of addition is sufficiently slow to allow the water phase to be completely incorporated in the silicone phase to provide a water-in-silicone emulsion having a substantially homogeneous appearance.

The make-up foundation composition of Example 9 provides the excellent sensory properties of an oil-in-silicone type foundation. The alkyl functionalized elastomer stabilizes the emulsion and gives a smooth, silky feel with even coverage.

EXAMPLE 10–12

The anhydrous emulsions of Example 10–12 are made by combining the listed components in the relative amounts (in pbw) set forth below in TABLE II.

TABLE II

| | | | |
|---|---|---|---|
| Silicone Phase | | | |
| Cyclopentasiloxane and dimethicone copolyol | 10 | 10 | 10 |
| Silicone elastomer of Example 1 | 10 | 10 | 10 |
| Organic Phase | | | |
| Butylene Glycol | 80 | — | — |
| Propylene Glycol | — | 80 | — |
| 2-methyl-1,3 Propane-Diol | — | — | 80 |

The components of the silicone phase are added to a mixing vessel in the order listed and mixed together with moderate agitation. The organic phase is then added to the silicone phase at a rate of addition is sufficiently slow to allow the organic phase to be completely incorporated in the silicone phase to provide a glycol-in-silicone emulsion having a substantially homogeneous appearance.

The anhydrous emulsions of Examples 10–12 provide an excellent non-tacky smooth feel.

EXAMPLE 13

The antiperspirant composition of Example 13 is made by combining the listed components in the relative amounts (in pbw) set forth below in TABLE III.

TABLE III

| | |
|---|---|
| Silicone elastomer of Example 1 | 80 |
| Aluminum Chlorohydrate | 20 |

Aluminum chlorohydrate is then added to the elastomer and mixed.

The antiperspirant composition of Example 13 illustrates the stabilization and thickening effects of the alkyl functionalized elastomer of the present invention. The resultant formula is creamy. Unlike most organic wax or clay thickened systems, this formulation shows no syneresis or separation with time. Additionally, the formula is smooth and easy to apply with virtually no visually detectable residue.

EXAMPLE 14

The clear anhydrous gel antiperspirant compositions of Example 10–12 are made by combining the listed components in the relative amounts (in pbw) set forth below in TABLE IV.

TABLE IV

| | |
|---|---|
| Silicone Phase | |
| Cyclomethicone and Dimethicone Copolyol | 2.5 |
| Silicone elastomer of Example 1 | 7.0 |
| Bis-Phenyl Propyl Dimethicone | 14.5 |
| Glycol Phase | |
| Polysorbate 80 | 0.25 |
| Propylene Glycol | 47.42 |
| 30% ZAG solution in Propylene Glycol (Westchlor A2Z 8106) | 23.33 |
| Ethanol | 5.0 |

The components of Part A are mixed together, reserving 3 percent of the propylene glycol for later use. The polysorbate 80 and ethanol are then dissolved in remaining propylene glycol. The ZAG solution is added to propylene glycol solution and mixed to form Part B. The refractive indices of Part A and Part B are each measured. The reserved propylene glycol is added by increments to part B to match the refractive index of Part B to Part A within ~0.00010 units. Once the desired refractive index match is obtained, Part B is slowly to Part A with moderate shear mixing. The agitation is gradually increased to high shear as the mixture thickens and then continued for ~5 minutes. The mixture is then homogenize 2 minutes in a high speed high shear mixer.

This example demonstrate a clear antiperspirant gel using an anhydrous glycol-in-silicone form. The formulation is stable, and with excellent sensory properties and provides a non-tacky, smooth and silky feel.

EXAMPLE 15

The oil-in-water gel composition of Example 13 is made by combining the listed components in the relative amounts (in pbw) set forth below in TABLE V.

TABLE V

| | |
|---|---|
| Part A | |
| water | 88.79 |
| Disodium EDTA | 0.03 |
| Citric Acid (10% solution) | 0.03 |
| Carbomer | 0.4 |

TABLE V-continued

| Part B | |
|---|---|
| 1,3 butylene glycol | 2.0 |
| glycerin (99%) | 3.5 |
| Part C | |
| Bis-Phenyl Propyl Dimethicone | 0.35 |
| Silicone elastomer of Example 1 | 3.0 |
| Part D | |
| Sodium Hydroxide (10% solution) | 1.6 |

The EDTA and citric acid are added to the water with moderate agitation until dissolved. The Carbomer is then to the water mixture slowly until dissolved. The components of B are then added to part A with moderate agitation. The components of art C are then added to the mixture of parts A and B in order listed. Part D is then added to the mixture with sweep agitation and pH adjusted to 7.2.

The oil-in-water gel composition of Example 15 illustrates the stabilization and detackification effects of elastomer in a carbomer thickened oil-in-water emulsion. The formulation imparts a silky non-tacky and light feel to the skin.

What is claimed is:

1. A silicone elastomer gel composition, comprising:
   (a) a liquid medium, comprising a silicone fluid, an organic liquid or a mixture thereof, and
   (b) a cross-linked, alkyl substituted silicone elastomer network swollen by the liquid medium, said network comprising a hydrosilylation reaction product of:
      (i) an alkenyl functional silicone compound;
      (ii) a silylhydride functional silicone compound; and
      (iii) one or more α,β-ethylenically unsaturated alkenes,
   wherein the alkenyl functional silicone compound comprises one or more compounds of the formula:

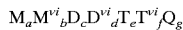

wherein:
   M is $R^1R^2R^3SiO_{1/2}$;
   $M^{vi}$ is $R^4R^5R^6SiO_{1/2}$;
   D is $R^7R^8SiO_{2/2}$;
   $D^{vi}$ is $R^9R^{10}SiO_{2/2}$;
   T is $R^{11}SiO_{3/2}$;
   $T^{vi}$ is $R^{12}SiO_{3/2}$; and
   Q is $SiO_{4/2}$;
   $R^1$, $R^2$, $R^3$ and $R^{11}$ are each independently alkyl, aryl or aralkyl;
   $R^4$ is a monovalent terminally unsaturated ($C_2$–$C_6$) hydrocarbon radical;
   $R^5$, $R^6$, $R^7$ and $R^8$ are each independently ($C_1$–$C_6$) alkyl;
   $R^9$ and $R^{12}$ are each independently monovalent terminally unsaturated hydrocarbon radicals;
   $R^{10}$ is a monovalent terminally unsaturated hydrocarbon radical, alkyl, aryl or aralkyl; and
   a, b, c, d, e, f and g are each integers wherein: b is 2; 100≦c≦2000; and a, d, e, f and g are each 0.

2. The composition of claim 1, wherein the composition comprises the cross-linked hydrosilylation reaction product of, based on 100 parts by weight of the combined alkenyl functional silicone compound, silylhydride functional silicone compound and α,β-ethylenically unsaturated alkenes, from 10 parts by weight to 99.9 parts by weight of the combined alkenyl functional silicone compound and silylhydride functional silicone compound and from greater than 0.1 parts by weight to 90 parts by weight of the one or more α,β-ethylenically unsaturated alkenes.

3. The composition of claim 1, wherein the silylhydride functional silicone compound comprises one or more compounds of the formula:

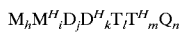

wherein:
   M is $R^1R^2R^3SiO_{1/2}$;
   $M^H$ is $R^{13}R^{14}R^{15}SiO_{1/2}$;
   D is $R^7R^8SiO_{2/2}$;
   $D^H$ is $R^{16}R^{17}SiO_{2/2}$;
   T is $R^{11}SiO_{3/2}$;
   $T^H$ is $R^{18}SiO_{3/2}$;
   Q is $SiO_{4/2}$;
   $R^1$, $R^2$, $R^3$, $R^7$, $R^8$ and $R^{11}$ are each independently alkyl, aryl or aralkyl;
   $R^{13}$, $R^{16}$ and $R^{18}$ are each independently H;
   $R^{14}$, $R^{15}$ and $R^{17}$ are each independently H, alkyl, aryl or aralkyl; and
   h, i, j, k, l, m, and n are each integers wherein h, i, l, m and n are each greater than or equal to 0 and less than or equal to 50, 0≦j≦2000, 0≦k≦200, and provided that (h+i)≦(2+31+3m+4n) and 1.5≦(i+k+m)≦200.

4. The composition of claim 3, wherein $R^{14}$ and $R^{15}$ are each independently ($C_1$–$C_6$)alkyl, and more preferably are each methyl; $R^{13}$ is H; 4≦i≦30; 1≦n≦15 and h, j, k, l and m are each 0.

5. The composition of claim 3, wherein $R^{14}$, $R^{15}$ and $R^{17}$ are each independently ($C_1$–$C_{12}$)alkyl, $R^{13}$ and $R^{16}$ are each H; h+i=2, 0≦j≦100, 2≦k≦100 and 1, m and n are each 0.

6. The composition of claim 1, wherein the composition is subjected to shear force to break the swollen silicone elastomer network into particles.

7. The silicone composition of claim 1, wherein the composition comprises, based on 100 parts by weight of the composition, from 1 part by weight to 99 parts by weight of the liquid medium, and from 1 part by weight to 99 parts by weight of the silicone elastomer network.

8. The silicone composition of claim 1, wherein the liquid medium comprises an organic liquid and a silicone fluid that is miscible with the organic liquid.

9. A personal care composition, comprising the silicone elastomer gel composition of claim 1.

10. The personal care composition of claim 9, wherein the composition is in the form of water-in-oil emulsion, an oil-in water emulsion or an anhydrous emulsion.

11. The personal care composition of claim 9, further comprising one or more components selected from emollients, pigments, vitamins, sunscreen compounds and sunblock compounds.

12. An antiperspirant composition comprising one or more active anti-perspirant agents and the silicone elastomer gel composition of claim 1.

13. A method for making a silicone elastomer gel composition, comprising contacting, under hydrosilylation conditions in the presence of a liquid medium, said liquid medium comprising a silicone fluid, an organic liquid or a mixture thereof, (i) an alkenyl functional silicone compound; (ii) a silylhydride functional silicone compound; and (iii) one or more α,β-unsaturated alkenes, wherein the alkenyl functional silicone compound comprises one or more compounds of the formula:

$$M_a M^{vi}_b D_c D^{vi}_d T_e T^{vi}_f Q_g$$

wherein:
M is $R^1R^2R^3SiO_{1/2}$;
$M^{vi}$ is $R^4R^5R^6SiO_{1/2}$;
D is $R^7R^8SiO_{2/2}$;
$D^{vi}$ is $R^9R^{10}SiO_{2/2}$;
T is $R^{11}SiO_{3/2}$;
$T^{vi}$ is $R^{12}SiO_{3/2}$; and
Q is $SiO_{4/2}$;
$R^1$, $R^2$, $R^3$ and $R^{11}$ are each independently alkyl, aryl or aralkyl;
$R^4$ is a monovalent terminally unsaturated ($C_2$–$C_6$) hydrocarbon radical;
$R^5$, $R^6$, $R^7$ and $R^8$ are each independently ($C_1$–$C_6$) alkyl;
$R^9$ and $R^{12}$ are each independently monovalent terminally unsaturated hydrocarbon radicals;
$R^{10}$ is a monovalent terminally unsaturated hydrocarbon radical, alkyl, aryl or aralkyl; and
a, b, c, d, e, f and g are each integers wherein: b is 2; $100 \leq c \leq 2000$; and a, d, e, f and g are each 0.

14. A silicone emulsion composition, comprising a silicone elastomer gel, said silicone elastomer gel comprising:
   (a) a liquid medium, comprising an emulsion of a first liquid phase and a second liquid phase, and
   (b) a cross-linked, alkyl substituted silicone elastomer network swollen by the liquid medium, said network comprising a hydrosilylation reaction product of:
      (i) an alkenyl functional silicone compound;
      (ii) a silylhydride functional silicone compound; and
      (iii) one or more α,β-ethylenically unsaturated alkenes,
   wherein the alkenyl functional silicone compound comprises one or more compounds of the formula:

$$M_a M^{vi}_b D_c D^{vi}_d T_e T^{vi}_f Q_g$$

wherein:
M is $R^1R^2R^3SiO_{1/2}$;
$M^{vi}$ is $R^4R^5R^6SiO_{1/2}$;
D is $R^7R^8SiO_{2/2}$;
$D^{vi}$ is $R^9R^{10}SiO_{2/2}$;
T is $R^{11}SiO_{3/2}$;
$T^{vi}$ is $R^{12}SiO_{3/2}$; and
Q is $SiO_{4/2}$;
$R^1$, $R^2$, $R^3$ and $R^{11}$ are each independently alkyl, aryl or aralkyl;
$R^4$ is a monovalent terminally unsaturated ($C_2$–$C_6$) hydrocarbon radical;
$R^5$, $R^6$, $R^7$ and $R^8$ are each independently ($C_1$–$C_6$) alkyl;
$R^9$ and $R^{12}$ are each independently monovalent terminally unsaturated hydrocarbon radicals;
$R^{10}$ is a monovalent terminally unsaturated hydrocarbon radical, alkyl, aryl or aralkyl; and
a, b, c, d, e, f and g are each integers wherein: b is 2; $100 \leq c \leq 2000$; and a, d, e, f and g are each 0.

15. The silicone emulsion of claim 14, wherein the first liquid phase comprises a first liquid, the second liquid phase comprises a second liquid and the composition comprises, based on 100 parts by weight of the combined amount of first and second liquids, from 0.1 parts by weight to 99.9 parts by weight of the first liquid, from 0.1 parts by weight to 99.9 parts by weight of the second liquid and, based on 100 parts by weight of the silicone emulsion, from 0.001 parts by weight to 75 parts by weight of the silicone elastomer.

16. The silicone emulsion of claim 15, wherein the first liquid comprises a silicone fluid, a substantially non-polar organic liquid or a mixture thereof and the second liquid comprises water, a substantially polar organic liquid or a mixture thereof.

17. The silicone emulsion of claim 15, wherein the first liquid comprises a silicone fluid, a substantially non-polar organic liquid, or a mixture thereof and the second liquid comprises a substantially polar organic liquid.

18. A silicone elastomer gel composition, comprising:
   (a) a liquid medium, comprising a silicone fluid, an organic liquid or a mixture thereof, and
   (b) a cross-linked, alkyl substituted silicone elastomer network swollen by the liquid medium, said network comprising a hydrosilylation reaction product of:
      (i) an alkenyl functional silicone compound;
      (ii) a silylhydride functional silicone compound; and
      (iv) one or more α,β-ethylenically unsaturated alkenes,
   wherein the silylhydride functional silicone compound comprises one or more compounds of the formula:

$$M_h M^H_i D_j D^H_k T_l T^H_m Q_n$$

wherein:
M is $R^1R^2R^3SiO_{1/2}$;
$M^H$ is $R^{13}R^{14}R^{15}SiO_{1/2}$;
D is $R^7R^8SiO_{2/2}$;
$D^H$ is $R^{16}R^{17}SiO_{2/2}$;
T is $R^{11}SiO_{3/2}$;
$T^H$ is $R^{18}SiO_{3/2}$;
Q is $SiO_{4/2}$;
$R^1$, $R^2$, $R^3$, $R^7$, $R^8$ and $R^{11}$ are each independently alkyl, aryl or aralkyl;
$R^{13}$, $R^{16}$ and $R^{18}$ are each independently H;
$R^{14}$ and $R^{15}$ are each independently ($C_1$–$C_6$)alkyl;
$R^{17}$ is H, alkyl, aryl or aralkyl; and
h, i, j, k, l, m, and n are each integers wherein $4 \leq i \leq 30$; $1 \leq n \leq 15$ and h, j, k, l and m are each 0.

19. The composition of claim 18, wherein the composition comprises the cross-linked hydrosilylation reaction product of, based on 100 parts by weight of the combined alkenyl functional silicone compound, silylhydride functional silicone compound and α,β-ethylenically unsaturated alkenes, from 10 parts by weight to 99.9 parts by weight of the combined alkenyl functional silicone compound and silylhydride functional silicone compound and from greater than 0.1 parts by weight to 90 parts by weight of the one or more α,β-ethylenically unsaturated alkenes.

20. The composition of claim 18, wherein the alkenyl functional silicone compound comprises one or more compounds of the formula:

$$M_a M^{vi}_b D_c D^{vi}_d T_e T^{vi}_f Q_g$$

wherein:
M is $R^1R^2R^3SiO_{1/2}$;
$M^{vi}$ is $R^4R^5R^6SiO_{1/2}$;

D is $R^7R^8SiO_{2/2}$;
$D^{vi}$ is $R^9R^{10}SiO_{2/2}$;
T is $R^{11}SiO_{3/2}$;
$T^{vi}$ is $R^{12}SiO_{3/2}$; and
Q is $SiO_{4/2}$;
$R^1, R^2, R^3, R^7, R^8$ and $R^{11}$ are each independently alkyl, aryl or aralkyl;
$R^4, R^9$ and $R^{12}$ are each independently monovalent terminally unsaturated hydrocarbon radicals;
$R^5, R^6$ and $R^{10}$ are each independently monovalent terminally unsaturated hydrocarbon radicals, alkyl, aryl or aralkyl;
a, b, c, d, e, f and g are each integers wherein: a, b, e, f, and g are each greater than or equal to 0 and less than or equal to 50, $0 \leq c \leq 2000$, $0 \leq d \leq 200$, and provided that: $(a+b) \leq (2+3e+3f+4g)$ and $1.5 \leq (b+d+f) \leq 200$.

21. The composition of claim 18, wherein $R^{14}$ and $R^{15}$ are methyl.

22. A personal care composition, comprising the silicone elastomer gel composition of claim 21.

23. The composition of claim 18, wherein the composition is subjected to shear force to break the swollen silicone elastomer network into particles.

24. The silicone composition of claim 18, wherein the composition comprises, based on 100 parts by weight of the composition, from 1 part by weight to 99 parts by weight of the liquid medium, and from 1 part by weight to 99 parts by weight of the silicone elastomer network.

25. The silicone composition of claim 18, wherein the liquid medium comprises an organic liquid and a silicone fluid that is miscible with the organic liquid.

26. A personal care composition, comprising the silicone elastomer gel composition of claim 18.

27. The personal care composition of claim 18, wherein the composition is in the form of water-in-oil emulsion, an oil-in water emulsion or an anhydrous emulsion.

28. The personal care composition of claim 18, further comprising one or more components selected from emollients, pigments, vitamins, sunscreen compounds and sunblock compounds.

29. An anti-perspirant composition comprising one or more active anti-perspirant agents and silicone elastomer gel composition of claim 18.

30. A method for making a silicone elastomer gel composition, comprising contacting, under hydrosilylation conditions in the presence of a liquid medium, said liquid medium comprising a silicone fluid, an organic liquid or a mixture thereof, (i) an alkenyl functional silicone compound; (ii) a silylhydride functional silicone compound; and (iii) one or more α,β-unsaturated alkenes,
wherein the silylhydride functional silicone compound comprises one or more compounds of the formula:

$$M_hM^H_iD_jD^H_kT_lT^H_mQ_n$$

wherein:
M is $R^1R^2R^3SiO_{1/2}$;
$M^H$ is $R^{13}R^{14}R^{15}SiO_{1/2}$;
D is $R^7R^8SiO_{2/2}$;
$D^H$ is $R^{16}R^{17}SiO_{2/2}$;
T is $R^{11}SiO_{3/2}$;
$T^H$ is $R^{18}SiO_{3/2}$;
Q is $SiO_{4/2}$;
$R^1, R^2, R^3, R^7, R^8$ and $R^{11}$ are each independently alkyl, aryl or aralkyl;
$R^{13}, R^{16}$ and $R^{18}$ are each independently H;
$R^{14}$ and $R^{15}$ are each independently $(C_1-C_6)$alkyl;
$R^{17}$ is H, alkyl, aryl or aralkyl; and
h, i, j, k, l, m, and n are each integers wherein $4 \leq i \leq 30$; $1 \leq n \leq 15$ and h, j, k, l and m are each 0.

31. A silicone emulsion composition, comprising a silicone elastomer gel, said silicone elastomer gel comprising:
(a) a liquid medium, comprising an emulsion of a first liquid phase and a second liquid phase, and
(b) a cross-linked, alkyl substituted silicone elastomer network swollen by the liquid medium, said network comprising a hydrosilylation reaction product of:
(i) an alkenyl functional silicone compound;
(ii) a silylhydride functional silicone compound; and
(iii) one or more α,β-ethylenically unsaturated alkenes,
wherein the silylhydride functional silicone compound comprises one or more compounds of the formula:

$$M_hM^H_iD_jD^H_kT_lT^H_mQ_n$$

wherein:
M is $R^1R^2R^3SiO_{1/2}$;
$M^H$ is $R^{13}R^{14}R^{15}SiO_{1/2}$;
D is $R^7R^8SiO_{2/2}$;
$D^H$ is $R^{16}R^{17}SiO_{2/2}$;
T is $R^{11}SiO_{3/2}$;
$T^H$ is $R^{18}SiO_{3/2}$;
Q is $SiO_{4/2}$;
$R^1, R^2, R^3, R^7, R^8$ and $R^{11}$ are each independently alkyl, aryl or aralkyl;
$R^{13}, R^{16}$ and $R^{18}$ are each independently H;
$R^{14}$ and $R^{15}$ are each independently $(C_1-C_6)$alkyl;
$R^{17}$ is H, alkyl, aryl or aralkyl; and
h, i, j, k, l, m, and n are each integers wherein $4 \leq i \leq 30$; $1 \leq n \leq 15$ and h, j, k, l and m are each 0.

32. The silicone emulsion of claim 31, wherein the first liquid phase comprises a first liquid, the second liquid phase comprises a second liquid and the composition comprises, based on 100 parts by weight of the combined amount of first and second liquids, from 0.1 parts by weight to 99.9 parts by weight of the first liquid, from 0.1 parts by weight to 99.9 parts by weight of the second liquid and, based on 100 parts by weight of the silicone emulsion, from 0.001 parts by weight to 75 parts by weight of the silicone elastomer.

33. The silicone emulsion of claim 32, wherein the first liquid comprises a silicone fluid, a substantially non-polar organic liquid or a mixture thereof and the second liquid comprises water, a substantially polar organic liquid or a mixture thereof.

34. The silicone emulsion of claim 32, wherein the first liquid comprises a silicone fluid, a substantially non-polar organic liquid, or a mixture thereof and the second liquid comprises a substantially polar organic liquid.

* * * * *